United States Patent [19]
Ishida et al.

[11] Patent Number: 5,389,550
[45] Date of Patent: Feb. 14, 1995

[54] ORGANIC SUBSTANCE ANALYZING METHOD AND APPARATUS USING PORTABLE CONSTRUCTION

[75] Inventors: Shigeaki Ishida, Kameoka; Hidetoshi Fujimori, Kyoto; Hideki Matsubayashi; Tsutomu Machihara, both of Funabashi, all of Japan

[73] Assignee: Japan National Oil Corporation, Tokyo, Japan

[21] Appl. No.: 146,109

[22] PCT Filed: Mar. 12, 1993

[86] PCT No.: PCT/JP92/00305
   § 371 Date: Nov. 10, 1993
   § 102(e) Date: Nov. 10, 1993

[87] PCT Pub. No.: WO93/18400
   PCT Pub. Date: Sep. 16, 1993

[30] Foreign Application Priority Data

Mar. 13, 1992 [JP] Japan .................. 4-089778

[51] Int. Cl.$^6$ .......................... G01N 33/24
[52] U.S. Cl. .................. 436/32; 436/157; 436/171; 422/80; 422/94; 373/112; 373/136; 110/203
[58] Field of Search ............ 436/29, 31, 32, 171, 436/155, 157; 422/78, 80, 94; 373/110, 112, 136; 110/203

[56] References Cited
U.S. PATENT DOCUMENTS

| | | | |
|---|---|---|---|
| 4,248,599 | 2/1981 | Mommessin et al. | 436/32 |
| 4,251,674 | 2/1981 | Callejas et al. | 585/272 |
| 4,360,359 | 11/1982 | Dehler | 436/28 |
| 4,578,356 | 3/1986 | Larter | 436/31 |
| 4,629,702 | 12/1986 | Fan | 436/32 |
| 5,286,651 | 2/1994 | Smith | 436/32 |

*Primary Examiner*—Nina Bhat
*Attorney, Agent, or Firm*—Morgan & Finnegan

[57] ABSTRACT

An organic substance analyzing method is disclosed. A sample container 21 charged with a granulated rock sample is installed in a thermal cracking furnace 1. The thermal cracking furnace 1 is connected to a vacuum suction line 27 to be evacuated until a substantial vacuum is created therein, whereupon the furnace is closed. The closed thermal cracking furnace is rapidly heated to a first temperature at which hydrocarbons are more or less cracked but inorganic carbonates are not decomposed. The thermal cracking furnace is maintained at this temperature for a fixed time and then is cooled to a temperature at which the hydrocarbons in the thermal cracking furnace do not react with air. Then the furnace is connected to an air supply line 29 and an exhaust line 35 to pass the produced gases in the furnace to a hydrocarbon detector 34 and a $CO_2$ detector 33. From the output signals therefrom, HC peak P1 and $CO_2$ peak P3 are found and recorded. The thermal cracking furnace 1 heated to a second temperature higher than the first temperature to repeat the steps of exhaustion, heating, cooling and measurement to find and record at least HC peak P2.

7 Claims, 3 Drawing Sheets

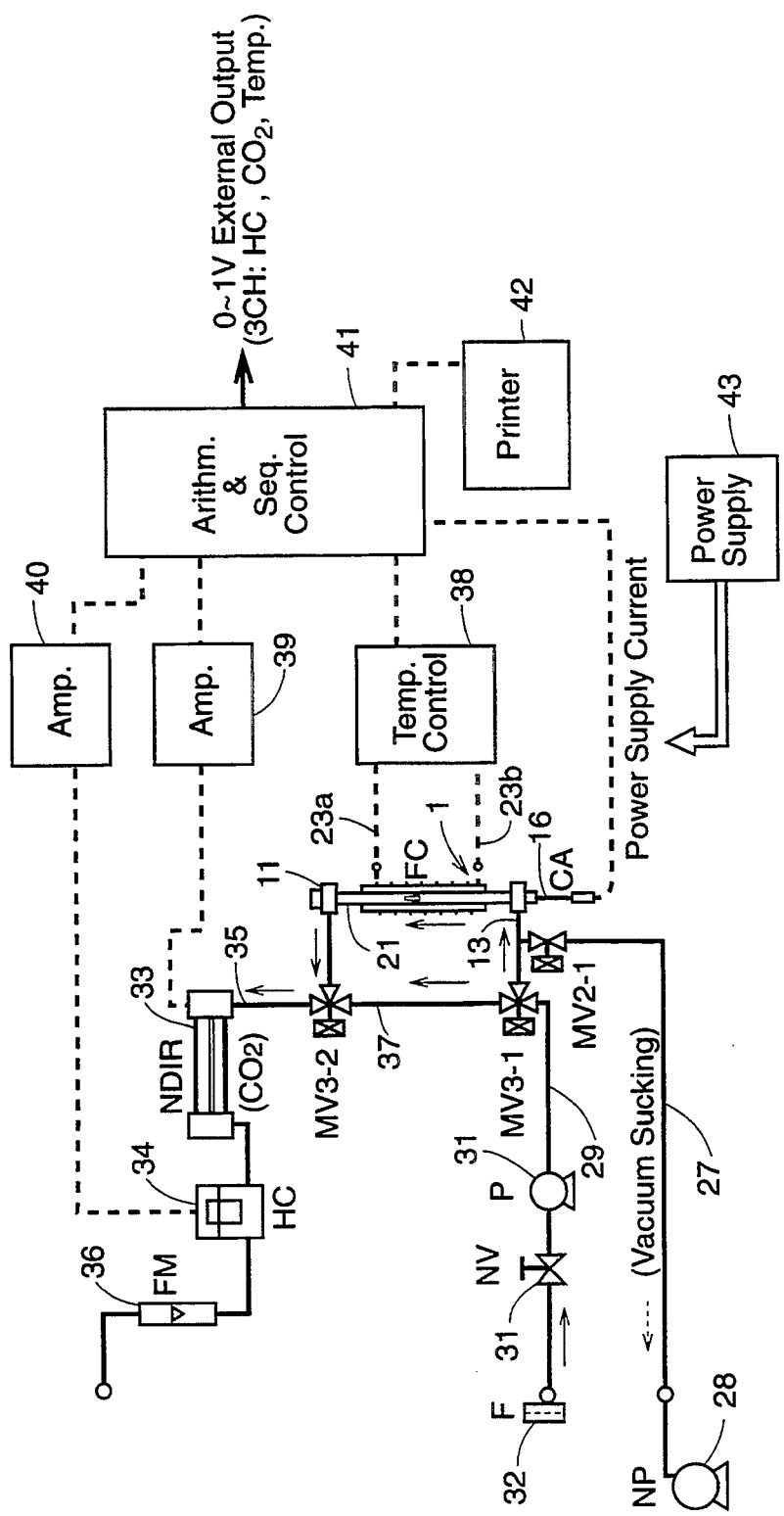

ORGANIC SUBSTANCE ANALYZING METHOD AND APPARATUS USING PORTABLE CONSTRUCTION

TECHNICAL FIELD

The present invention relates to an organic substance analyzing method and apparatus, and particularly it relates to an analyzer of small-sized and portable construction for rapidly evaluating the potential of petroleum source rock in the field.

BACKGROUND ART

A typical analyzer of fixed indoor type for evaluating the potential of petroleum source rock is adapted to analyze hydrocarbons and $CO_2$ evolved by thermal cracking of kerogen (insoluble high molecular organic substances in sediments are called "kerogen") in source rock; thus, it operates on the principle of rapidly heating about 100 mg of source rock sample in He stream from room temperature to 250° C., detecting the known hydrocarbons evaporating from the sample as an S1 peak by a hydrogen flame ionization detector (FID), heating the sample to about 550° C. at a heating rate of 25° C./min and detecting also by FID the hydrocarbons evolved by thermal cracking as an S2 peak. On the other hand, some of the thermally cracked gases flow as a branch stream to a $CO_2$ trap, where $CO_2$ being evolved at temperatures between 250° C. and 390° C. is arrested and then it is detected as a peak S3 by a gas chromatograph connected to a heat conductivity detector. In addition it has been generally accepted that since $CO_2$ is evolved by decomposition of inorganic carbonates at temperatures above 390° C., it suffices to detect the amount of $CO_2$ being evolved from organic carbonates as far as $CO_2$ in kerogen analysis is concerned. The type of kerogen can be determined from S1, S2, S3 and the peak temperature (Tmax) at which S2 is obtained in such analysis.

However, the apparatus described above is designed to be used in laboratories, requiring complicated control operation and using He gas requiring a steel gas cylinder and $H_2$ gas requiring a steel gas cylinder and liable to explode; thus, it is not suitable for use in the field. Therefore, at present, all of the samples taken are transferred to a location where such apparatus is installed (sometimes they are sent abroad) while it is still unknown whether or not they are worthy of analysis. This should be called a very wasteful analytical method from the standpoint of efficiency of analysis.

There is a recently developed portable measuring apparatus known as "source rock analyzer". This portable apparatus operates on the principle of using two large and small sieves (4.0 mm-5 mesh and 3.5 mm-6 mesh) for sorting rock sample particles taken in chip form, placing them in a thermal cracking furnace in the form of a small-sized crucible, instantaneously heating them in an air atmosphere to about 700° C. to evolve hydrocarbons, detecting said hydrocarbons by a contact combustion type gas sensor, and evaluating the amounts of organic substances contained in the sample in two-class evaluation (lean/rich decision).

This portable apparatus, featured as a small-sized thermal cracking furnace, has merits that (1) the analyzing time is shortened and that (2) the capacity of shearer is low and hence the battery is small-sized, resulting in the entire apparatus being small in size and light in weight, and it is suitable for use in the field. In a performance aspect, it has the following demerits.

(1) The rapid heating of a sample in an air atmosphere causes some of the hydrocarbons evolved to be burnt, leading to errors in measurement. At the same time, the $CO_2$ produced by combustion join the $CO_2$ produced by thermal cracking, making it impossible to identify these gases;

(2) Even if chip-like sample particles are sifted, their variations in weight are still great, affecting the measurement of hydrocarbons; and (3) The thermal cracking furnace is in the form of a crucible, with a heater wound naked on the inner surface, so that there is a difference in the attained temperature of the sample particles between the time the sample particles in the crucible are contacted with, the heater and the time they are not contacted, so that the amount of hydrocarbons produced differs from place to place.

DISCLOSURE OF THE INVENTION

The present invention relates to a portable analyzing apparatus of the type utilizing air, not using a special steel gas cylinder, and is intended to provide an organic substance analyzing method and apparatus which, when it is desired to analyze source rock in the field where it is mined, are adapted to relatively accurately and quickly analyze hydrocarbons (HC peaks P1 and P2) and $CO_2$ (not including $CO_2$ produced by decomposition of inorganic carbonates) contained in a sample and provide potential evaluation in 4–5 classes for each component and find hydrocarbon/$CO_2$ ratio per unit weight.

To achieve the object described above, the present invention provides an insoluble organic substance analyzing method using a portable construction including a hydrocarbon thermal cracking furnace adapted to be selectively connected to a vacuum sucking line and an air supplying line and also to an exhaust line for exhaust corresponding to air supply, and a hydrocarbon detector and a $CO_2$ detector which are placed in said exhaust line, said method comprising the steps of a) placing a sample container charged with a granulated rock sample in said thermal cracking furnace maintained at a temperature above room temperature but below 100° C., connecting said thermal cracking furnace to said vacuum sucking line, evacuating the furnace until a substantial vacuum state is established therein, and tightly closing the furnace, b) quickly heating said closed thermal cracking furnace from said temperature to a first temperature which is effective for evaporation and thermal cracking of some of the organic substances but which is not effective for decomposition of inorganic carbonates, said furnace being maintained at this temperature for a fixed period of time, c) cooling said thermal cracking furnace to a temperature at which the hydrocarbons in the furnace do not react with air, and connecting it to said air supplying line and said exhaust line to allow the produced gases in the furnace to flow into the hydrocarbon detector and $CO_2$ detector to compute the HC peak P1 and $CO_2$ peak P3 from output signals therefrom, d) connecting said thermal cracking furnace again to the vacuum sucking line, evacuating the furnace, tightly closing the furnace, and rapidly heating the furnace to a second temperature higher than said first temperature to effect substantial thermal cracking of the insoluble organic substances, said furnace being maintained at this temperature for a fixed period of time, e) cooling said thermal cracking furnace to a temperature at which the hydrocarbons in the furnace do not react with air, and connecting it to said air supplying line and said exhaust line to allow the produced gases in the furnace to flow into the hydrocarbon detector and $CO_2$ detector to find at least the HC peak P2 from the output signals therefrom and record it, and f) deciding the types and amounts of organic substances from the sizes of said peaks P1, P2 and P3.

To execute said method, the present invention also provides an insoluble organic substance analyzing apparatus using a portable construction, comprising;

- a hydrocarbon thermal cracking furnace having a heater, adapted to be selectively connected to a vacuum sucking line leading to a vacuum source and an air supplying line leading to an air supply source, said furnace being also connectible to an exhaust line in response to air supply.
- a temperature control circuit for controlling the energization of the heater of said thermal cracking furnace,
- a detecting system consisting of a hydrocarbon detector and $CO_2$ detector which are placed in said exhaust line,
- a computation and sequence control unit electrically connected to valve means for lines associated with said thermal cracking furnace, to said temperature control circuit, and to said hydrocarbon detector and $CO_2$ detector, said control unit performing the steps of (1) initializing said thermal cracking furnace at a temperature below 100° C., (2) rapidly heating said thermal cracking furnace in a closed vacuum state from the initial set temperature to a first temperature which does not decompose inorganic carbonates, and maintaining the furnace at this temperature, (3) rapidly heating said thermal cracking furnace in its closed vacuum state from a cooling temperature lower than said first temperature to a temperature higher than said first temperature, and maintaining said furnace at this temperature, (4) cooling said thermal cracking furnace from said first or second temperature to a temperature at which hydrocarbons are insensitive to air, and connecting said furnace to the air supplying line and exhaust line, (5) recording at least HC peaks P1 and P2 and $CO_2$ peak P3 of the output signals generated from the hydrocarbon detector and $CO_2$ detector in said exhaust line during line connection in the step (4) and deciding the types and amounts of the organic substances from the hydrocarbon amount P1+P2 and $CO_2$ amount P3.

According to the method and apparatus described above, since thermal cracking is effected in the closed vacuum state, the operation is not influenced by combustion based on the oxygen in air and errors in the measurement of hydrocarbons can be reduced while measurement of $CO_2$ becomes possible. More particularly, after each of the thermal cracking operations at 390° C. and 550° C., the thermal cracking furnace is cooled to a temperature at which the hydrocarbons in the furnace do not react with air (or do not burn) and then they are transferred to the measuring system by air. Thus, in the apparatus of the present invention, special inert gases (He, $N_2$ and others) for passage or hydrogen gas for FID are not used, the apparatus is safe and light in weight and convenient Further, since a granulated sample can be sifted to obtain particles within sufficiently narrow particle size range, if the level to which particles are packed into a sample container is constant, relatively accurate sampling based on sample weight referring to the level is possible.

BRIEF DESCRIPTION OF THE DRAWINGS

FIG. 2 is a longitudinal sectional view showing a sample container to be placed in the thermal cracking furnace of FIG. 1;

FIG. 3 is a diagram showing a channel arrangement and electric circuit connection incorporated in the thermal cracking furnace of FIG. 1.

BEST MODE FOR CARRYING OUT THE INVENTION

Figure 1:
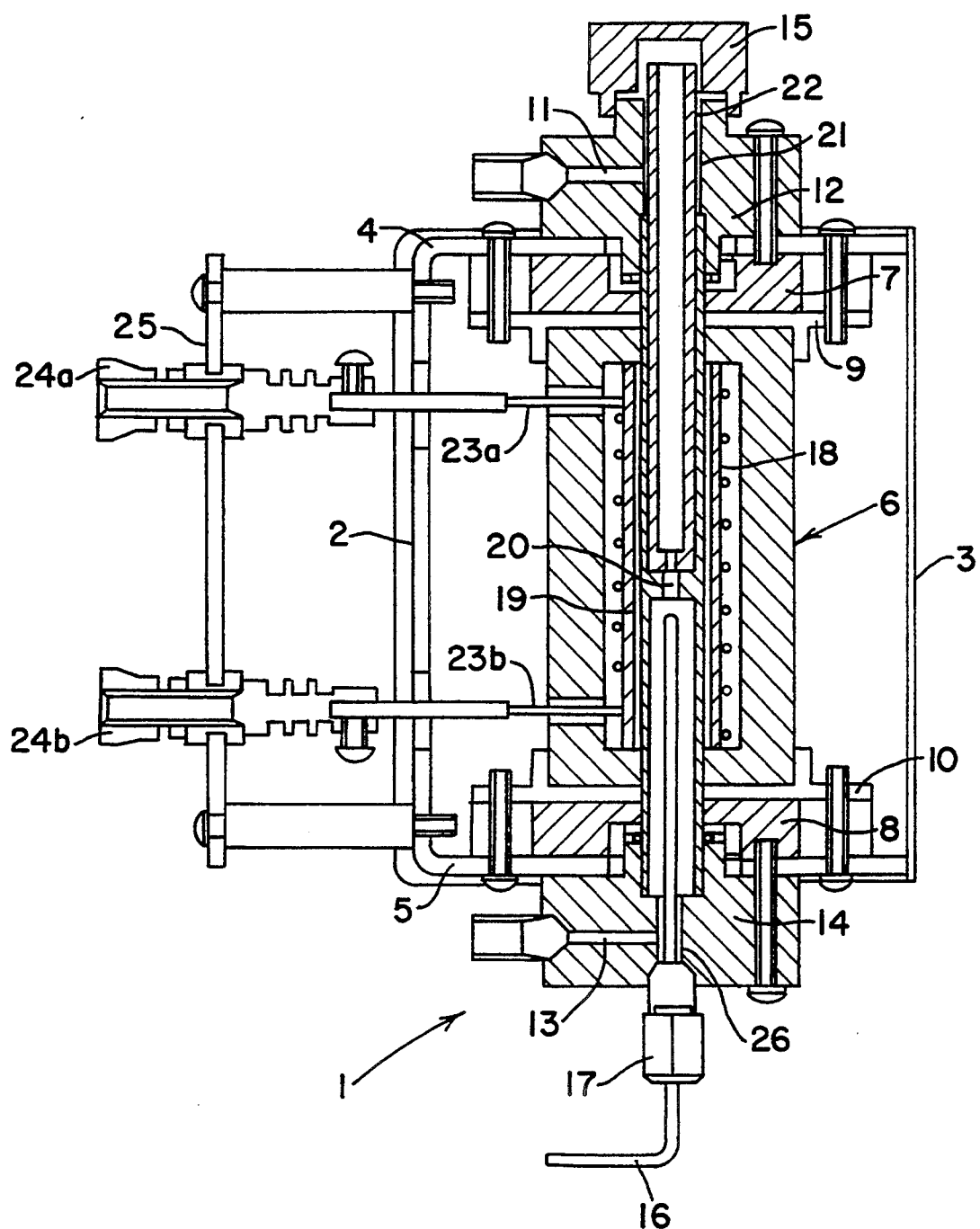
FIG. 1 is a longitudinal sectional view of a small-sized thermal cracking furnace in an embodiment of the present invention.

An apparatus according to the invention will now be described with reference to FIGS. 1 through 3. As shown in FIG. 1, a small-sized thermal cracking furnace 1 has cylindrical furnace body 6 held in a frame structure comprising side plates 2 and 3 and upper and lower plates 4 and 5 connected to the upper and lower ends of the side plate 2. More particularly, the upper and lower plates 4 and 5 hold upper and lower end plates 9 and 10 by upper and lower spacers 7 and 8, said upper and lower end plates 9 and 10 holding the upper and lower end surfaces of the furnace body 6 to maintain the latter in the upright state. An upper block 12 having an exhaust port 11 and a lower block 14 having an air inlet-outlet port 13 are fixed to the outer side (upper side) of the upper plate 4, with a cap 15 mounted on the upper end of the upper block 12. Mounted on the lower end of the lower block 14 is a screw plug 17 having a CA wire serving as a temperature sensor. Disposed in the cylindrical chamber in the furnace body 6 are an outer tube 18 and an inner tube 19 axially disposed inside said outer pipe with a slight clearance therebetween. The upper and lower ends of the inner tube 19 project successively through the upper and lower portions of the furnace body 6, tile end plates 9 and 10, the upper and lower spacers 7 and 8, and the upper and lower plates 4 and 5 and into the upper and lower blocks 12 and 14. The central portion of the inner tube 19 is formed with a node having a narrow hole 20 extending along the axis, the node serving as a bottom surface for receiving a thin tube-like sample container 21 in the upper half. The upper block 12 is formed with a reception hole 22 for receiving the sample container 21, and the upper end of the sample container 21 projecting beyond the upper block 12 is covered with a cap 15. The sample container 21 and inner and outer tubes 19 and 18 are quartz tubes, with a heater wire, for example, a Kanthal wire, wound around the outer tube 18, the opposite ends 23a and 23b of said heater being led out of the furnace body 6 through the side plate 2. A terminal plate 25 having terminals 24a and 24b mounted thereon for connecting and holding the opposite ends of the heater is supported by the side plate 2 in projecting relation thereto. The lower surface of the lower block 14 is formed with an axial hole 26 communicating with the air inlet-outlet port 13, and the front end of the temperature sensor 16 is sufficiently smaller than the inner diameter of the axial hole 26 for the air inlet-outlet port 13 to lead through the space around the temperature sensor 16 in the axial hole 26 to the lower portion of the inner tube 19 and then through the intermediate axial hole 20 to the sample container 21.

FIG. 2 shows the sample container in detail, In the preferred embodiment, the sample container 21 made of quartz has a length of 67 mm, an outer diameter of 5.5 mm and an inner diameter of 3.5 mm and has a communication hole 21a of 1.0 mm in diameter in the lower end. The presence of said communication hole 21a provides the communicating relation with the lower portion of the inner tube 19.

FIG. 3 is a diagram showing the piping connection and electrical connection of said thermal cracking furnace 1. The air inlet-outlet port 13 of the thermal cracking furnace has a vacuum pump 28 connected thereto through a line 27 and a diaphragm pump 30 connected thereto through a line 29. The line 27 is a vacuum suction line and the line 29 is an air supply line, these lines being connected to the air inlet-outlet port 13 through solenoid valves MV 2-1 and MV 3-1, respectively. The air supply line 29 has a flow control needle valve 31 placed therein upstream of the diaphragm pump 30 and an air filter 32 placed therein at the upstream line end thereof to serve as an air intake port.

The exhaust port 11 of the thermal cracking furnace 1 has connected thereto, in this case, an exhaust line 35 having placed therein a $CO_2$ detector 33 of the infrared nondispersion type and a hydrocarbon (HC) detector 34 in the form of a contact type combustion sensor. A flow meter 36 is placed in the downstream region of the exhaust line 35, and in the upstream region thereof a solenoid valve MV 3-2 is connected to the exhaust port 11 of the thermal cracking surface 1. This solenoid valve MV 3-2 and the solenoid valve MV 3-1 in the air supply line are three-way solenoid valves, the remaining one flow port of one valve being connected to such port of the other by a bypass line 37, so that air introduced from the diaphragm pump 30 is led directly to the exhaust line 35 through said bypass line 37.

The channel arrangement in the embodiment described above is controlled by the electrical circuit connection which follow. The numeral 38 denotes a temperature control circuit for passing a control current between the heater terminals 23a and 23b of the thermal cracking furnace 1; 39 denotes an amplifier for receiving the output signal from the $CO_2$ detector 33; 40 denotes an amplifier for receiving the output from the HC detector 34; and 41 denotes an arithmetic and sequence control unit for performing switching control of the solenoid valves MV 2-1, MV 3-1, MV 3-2, performing selective drive control of the vacuum pump 28 and diaphragm pump 30 and executing the function of controlling the temperature control circuit 38 while monitoring temperature signals from the temperature sensor 16 and the function of storing and computing output signals from the amplifiers 39 and 40 during exhaust from the thermal cracking furnace and measurement. A printer 42 is connected to the arithmetic and sequence control unit 41 to process output signals from the detectors and record the computed values. A power supply unit 43 serves to supply electric energy to the electric system described above, and is connected directly to 100 volt AC or required source voltages are derived via a DC/AC converter or the like from a contained battery.

The organic substance analyzing method of the present invention is embodied in the following manner using the above apparatus.

(1) Charging of Rock Sample into Sample Container 21.

To prepare a rock sample, grits or chips are granulated by a hammer, passed through two sieves of 1 mm mesh and 0.5 mm mesh, respectively to provide a sample having a diameter range of 0.5-1 mm, said sample being placed in the sample container 21 to a given height. In addition, the particle size may be further reduced by pulverization.

(2) Installation in Small-Sized Thermal Cracking Furnace.

The sample container 21 charged with the sample is installed in the small-sized thermal cracking furnace 1 as shown in FIG. 1, with the cap 15 applied thereto. In addition, after the power supply 43 (see FIG. 3) has been turned on, the thermal cracking furnace 1 reaches an initial set temperature of 50°-100° C. and is maintained at this temperature.

(3) Evacuation of Furnace and Base Line Setting

In the channel arrangement shown in FIG. 3, the two-way solenoid valve MV 2-1 is opened and the three-way solenoid valves MV 3-1 and MV 3-2 on the inlet and outlet sides of the thermal cracking furnace 1 are closed, the vacuum pump 28 alone is connected to evacuate the furnace until its internal pressure is about 1 torr or less, for example, whereupon the two-way solenoid valve MV 2-1 is closed, thereby establishing the vacuum closed state.

On the other hand, the diaphragm pump 30 is driven to draw the open air through the air filter 32, which air, while being controlled to a fixed flow rate by the needle valve 31, is fed successively through the three-way solenoid valve MV 3-1, the bypass line 37 and the three-way solenoid valve MV 3-2 and into the $CO_2$ detector 33 and hydrocarbon detector 34. The respective output states of the detectors are transmitted to the control unit 41 through the amplifiers 39 and 40 to form pneumatic base line signals. In this case, the two detectors 33 and 34 have been placed in series in the exhaust line 35, but if the downstream detector is influenced by the upstream detector, they will be connected in parallel.

(4) Thermal Cracking at Low Temperature

The thermal cracking furnace 1 is then rapidly heated from the initial set temperature to 390° C. and is maintained at this temperature for a fixed time, and then cooled. At 390° C. under vacuum, thermal cracking takes place in the sample in the thermal cracking furnace, producing hydrocarbons and $CO_2$, diffusing the products into the closed passages communicated with the furnace in this low temperature thermal cracking, there is no evolution of $CO_2$ due to decomposition of inorganic carbonates, as described above.

(5) Cooling and Measurement

The thermal cracking furnace 1 is cooled to the temperature at which even if the evolved hydrocarbons are contacted with air, they will not burn, and then the three-way solenoid valves MV 3-1 and MV 3-2 are switched to the thermal cracking furnace side to introduce the produced gases in the furnace into the detectors 33 and 34. At the respective detectors, hydrocarbon peak (P1) and $CO_2$ peak (P3) and the respective peak areas are computed in the arithmetic and sequence control unit 41.

(6) Thermal Cracking at High Temperature

Again, as described in Paragraph (2), after the furnace has been evacuated, it is rapidly heated to 550° C. and is maintained at this temperature for a fixed time, and then cooled. In this state in the thermal cracking furnace, thermal cracking further proceeds under vacuum and the produced hydrocarbons and $CO_2$ diffuse into the enclosed path.

(7) Cooling and Measurement

After the thermal cracking furnace has fully been cooled, as in the process (5), air is passed, whereupon hydrocarbon peak (P2) and $CO_2$ peak (P4) are obtained. In this case, the area of P2 alone is computed.

Figure 4:
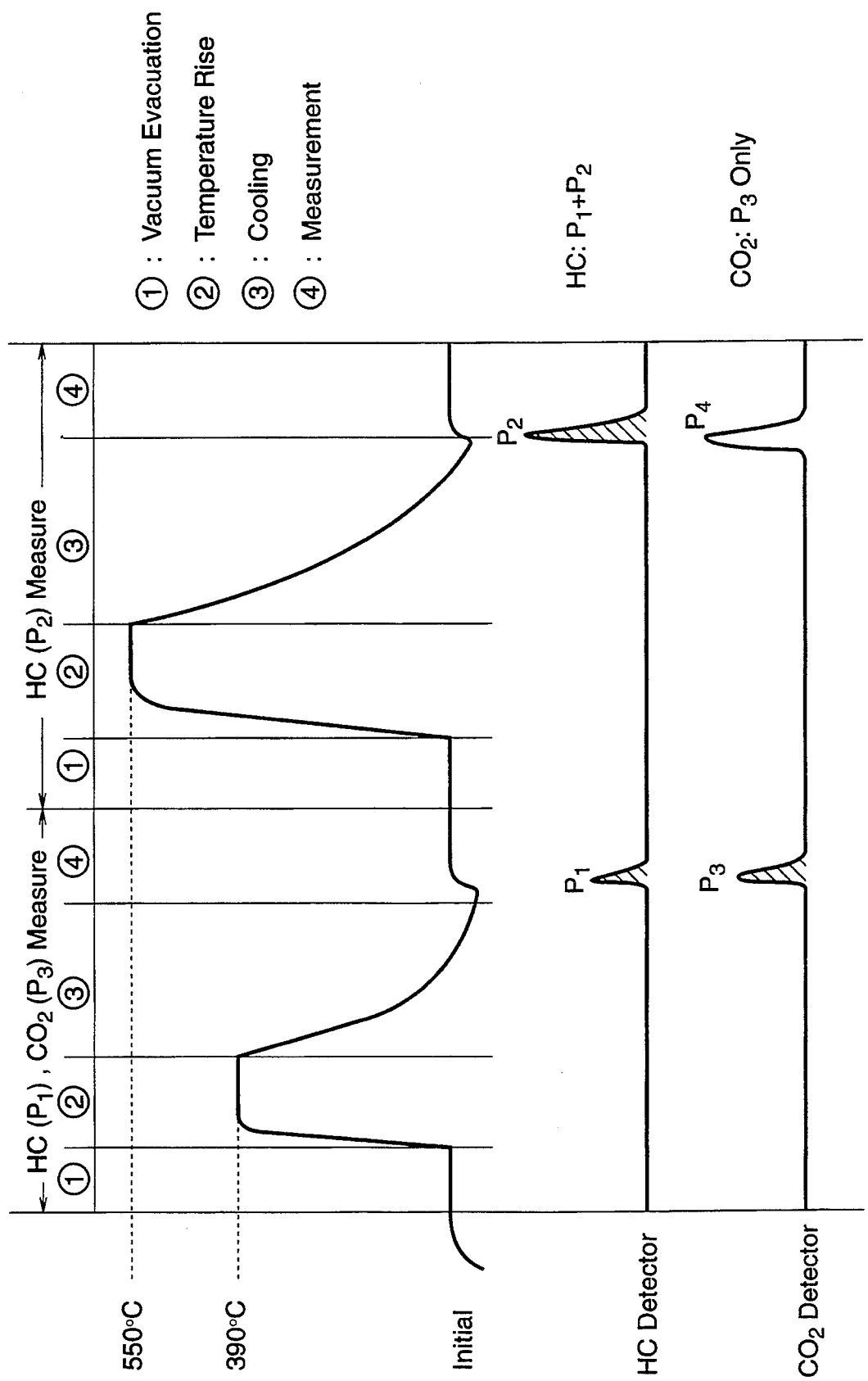
FIG. 4 is a graph showing analysis peaks (HC and $OO_2$ measurements) according to the apparatus of the invention.

The temperatures in the thermal cracking furnace and the peak detections in the respective steps described above are as shown in FIG. 4.

(8) Potential Evaluation

The amounts of components contained per unit weight of sample (mg/g) are found from the areas (as to hydrocarbons, P1+P2, and as to $CO_2$, P3 alone) in the arithmetic and sequence control unit 41 and from calibration curves preset for standard substances. The hydrocarbon and $CO_2$ contents and their ratio (H/C) are printed by the small-sized printer 42 and simulteneously the potential evaluation for the sample is provided by potential evaluation lamps (provided for indicating 4–5 classes, for example).

In addition, in this embodiment, the hydrocarbon detector is a contact combustion type sensor and the $CO_2$ detector is a nondispersion type infrared detector; however, one or both of them may be replaced by a semiconductor type.

In the apparatus of the embodiment, after the sample container 21 has been set, a series of operations up to potential evaluation have been automatically sequentially performed, but if this sequence is changed, analysis of hydrocarbons alone of $CO_2$ alone can be easily made.

Since the present invention is arranged in the manner described above, as compared with the conventional passage type thermal cracking apparatus (inert gas carrier type thermal cracking-analyzing apparatus), the peak shapes of components are better as they are sharp with less tailing. That is, in the case of the conventional passage type thermal cracking apparatus, even a slight variation in temperature during thermal cracking process can change the amount of produced gases, reflecting the peak shape and adversely affecting the reproducibility. In the technique of the present invention, however, even if there is a slight variation in temperature during thermal cracking process, the thermal cracking is averaged and this result appears as the size of the peak; thus, there is little dead space in the path to the detectors, a fact which seems to contribute to a sharp peak shape with less tailing.

INDUSTRIAL APPLICABILITY

As has so far been described, in the present invention, since thermal cracking is performed in the vacuum sealed state, it is not influenced by combustion due to the oxygen in air. Therefore, there is little error in the determination of the amount of hydrocarbons produced and the measurement of $CO_2$ has become possible. Further, since the produced gases are discharged after they have been cooled in the vacuum sealed state, there is no need for a special inert gas as a carrier gas; however, the two conditions, correctness of analysis and portability, which have heretofore been incompatible, are now made compatible.

There are some source rock samples which, when thermally cracked, produce high boiling point components which coagulate at temperatures below the thermal cracking temperature, adhering to the path. However, by lengthening the sample container and placing it upright, the coagulated components adhere to the upper region of the sample container where temperature hardly rises, while the other gases can be continuously analyzed through exchange of sample containers or by washing without contaminating the gas channel system.

In various job sites, in the case where the weight measurement of a sample by an electronic balance is impossible, since the sample particles sorted to have a fixed particle size are charged into an elongated sample container, the weight range is relatively stable; for example, for 100 mg, the accuracy can be within $\pm 5\%$.

In addition, the apparatus of the present invention, as compared with the recently employed portable type analyzing apparatus, has the merit of greatly improved accuracy, but it has the demerit of a more or less increase in size, as it requires an increased heater capacity and a vacuum pump. However, the apparatus of the invention is of such shape and weight that it can be carried on a light van or a wagon car and can be powered by an automobile battery. Thus, the apparatus is highly practical, suitable for use in the field.

What is claimed is:

1. An insoluble organic substance analyzing method using a portable construction including a hydrocarbon thermal cracking furnace adapted to be selectively connected to a vacuum sucking line and an air supplying line and also to an exhaust line for exhaust corresponding to air supply, and a hydrocarbon detector and a $CO_2$ detector which are placed in said exhaust line, said method comprising the steps of a) placing sample container filled with a granulated rock sample in said thermal cracking furnace maintained at a temperature above room temperature but below 100° C., connecting said thermal cracking furnace to said vacuum sucking line, evacuating the furnace until a substantial vacuum state is established therein, and tightly closing the furnace, b) quickly heating said closed thermal cracking furnace from said temperature to a first temperature which is effective for evaporation and thermal cracking of some of the organic substances but which is not effective for decomposition of inorganic carbonates, said furnace being maintained at this temperature for a fixed period of time, c) cooling said thermal cracking furnace to a temperature at which the hydrocarbons in the furnace do not react with air, and connecting it to said air supplying line and said exhaust line to allow the produced gases in the furnace to flow into the hydrocarbon detector and $CO_2$ detector to compute the HC peak P1 and $CO_2$ peak P3 from output signals therefrom, d) connecting said thermal cracking furnace again to the vacuum sucking line, evacuating the furnace, tightly closing the furnace, and rapidly heating the furnace to a second temperature higher than said first temperature to effect substantial thermal cracking of the insoluble organic substances, said furnace being maintained at this temperature for a fixed period of time, e) cooling said thermal cracking furnace to a temperature at which the hydrocarbons in the furnace do not react with air, and connecting it to said air supplying line and said exhaust line to allow the produced gases in the furnace to flow into the hydrocarbon detector and $CO_2$ detector to find at least the HC peak P2 from the output signals therefrom and record it, and f) deciding the types and amounts of organic substances from the sizes of said peaks P1, P2 and P3.

2. A method as set forth in claim 1, characterized in that granulated sample particles are sorted to have particle size range of 0.5–1.0 mm and this sample is charged into said sample container to a predetermined level.

3. A method as set forth in claim 1, characterized in that said first and second temperatures are 390° C. and respectively.

4. An insoluble organic substance analyzing apparatus using a portable construction, comprising;

a hydrocarbon thermal cracking furnace having a heater, adapted to be selectively connected to a vacuum sucking line leading to a vacuum source and an air supplying line leading to an air supply source, said furnace being also connectible to an exhaust line in response to air supply, a temperature control circuit for controlling the energization of the heater of said thermal cracking furnace, a detecting system consisting of a hydrocarbon detector and $CO_2$ detector which are placed in said exhaust line, a computation and sequence control unit electrically connected to valve means for lines associated with said thermal cracking furnace, to said temperature control circuit, and to said hydrocarbon detector and $CO_2$ detector, said control unit performing the steps of (1) initializing said thermal cracking furnace at a temperature below 100° C., (2) rapidly heating said thermal cracking furnace in a closed vacuum state from the initial set temperature to a first temperature which does not decompose inorganic carbonates, and maintaining the furnace at this temperature, (3) rapidly heating said thermal cracking furnace in the closed vacuum state from a cooling temperature lower than said first temperature to a temperature higher than said first temperature, and maintaining said furnace at this temperature, (4) cooling said thermal cracking furnace from said first or second temperature to a temperature at which hydrocarbons are insensitive to air, and connecting said furnace to the air supplying line and exhaust line, (5) recording at least HC peaks P1 and P2 and $CO_2$ peak P3 of the output signals generated from the hydrocarbon detector and $CO_2$ detector in said exhaust line during line connection in the step (4) and deciding the types and amounts of the organic substances from the hydrocarbon amount P1+P2 and $CO_2$ amount P3.

5. An apparatus as set forth in claim 4, characterized in that the sample container to be installed in the thermal cracking furnace is a tube designed so that the sample storage level is visible, said tube having a channel construction adapted to communicate with said vacuum line, said air supply line, and exhaust line when it is installed in said furnace.

6. An apparatus as set forth in claim 4, characterized in that said hydrocarbon detector is a contact combustion type hydrocarbon detector and said $CO_2$ detector is a nondispersion type infrared detector.

7. An apparatus as set forth in claim 4, characterized in that said apparatus includes an air bypass line disposed between the air supply line connection port and the exhaust line connection port of said thermal cracking furnace, and also includes a thermal cracking furnace-bypass line switching valve means, so that the bypass line is opened and air is passed to said hydrocarbon detector and $CO_2$ detector in said exhaust line, thereby establishing base lines at the measurements in said hydrocarbon detector and $CO_2$ detector.

* * * * *